(12) United States Patent
Perkins et al.

(10) Patent No.: US 8,787,609 B2
(45) Date of Patent: Jul. 22, 2014

(54) EARDRUM IMPLANTABLE DEVICES FOR HEARING SYSTEMS AND METHODS

(71) Applicant: EarLens Corporation, Redwood City, CA (US)

(72) Inventors: Rodney C. Perkins, Woodside, CA (US); Sunil Puria, Sunnyvale, CA (US)

(73) Assignee: EarLens Corporation, Redwood City, CA (US)

( * ) Notice: Subject to any disclaimer, the term of this patent is extended or adjusted under 35 U.S.C. 154(b) by 0 days.

(21) Appl. No.: 13/770,106

(22) Filed: Feb. 19, 2013

(65) Prior Publication Data

US 2013/0315428 A1    Nov. 28, 2013

Related U.S. Application Data

(62) Division of application No. 12/818,449, filed on Jun. 18, 2010, now Pat. No. 8,401,214.

(60) Provisional application No. 61/218,380, filed on Jun. 18, 2009.

(51) Int. Cl.
*H04R 25/00* (2006.01)
*H04R 1/10* (2006.01)

(52) U.S. Cl.
CPC ............... *H04R 25/606* (2013.01); *H04R 1/10* (2013.01); *H04R 25/60* (2013.01); *H04R 2460/13* (2013.01)
USPC ......................................... 381/326

(58) Field of Classification Search
CPC .. H04R 2460/13; H04R 25/606; H04R 25/60; H04R 1/10
USPC ............................................. 381/326
See application file for complete search history.

(56) References Cited

U.S. PATENT DOCUMENTS 3,209,082 A    9/1965  McCarrell et al.
3,440,314 A    4/1969  Frisch
(Continued)

FOREIGN PATENT DOCUMENTS

DE    2044870 A1    3/1972
DE    3243850 A1    5/1984
(Continued)

OTHER PUBLICATIONS

U.S. Appl. No. 60/702,532, filed Jul. 25, 2005, Aljuri.
(Continued)

*Primary Examiner* — Jianchun Qin
(74) *Attorney, Agent, or Firm* — Wilson Sonsini Goodrich & Rosati

(57) ABSTRACT

An implantable device is configured for placement in the eardrum to transmit an audio signal to a user. The device may be configured to improve transmission of an electromagnetic signal from an input assembly on a lateral side of eardrum to an output assembly positioned on a medial side of the eardrum, for example at least partially in the middle ear of the user. The output assembly may comprise a transducer or at least two electrodes configured to stimulate the cochlea, for example. The device may include an opening to transmit the light signal or an optic to transmit the light signal. Alternatively the device may be configured to support a transducer of the output assembly with the eardrum when the device is implanted in the eardrum, such that the eardrum vibrates in response to the signal electromagnetic signal. The electromagnetic signal may include light energy.

13 Claims, 7 Drawing Sheets

(56) References Cited

U.S. PATENT DOCUMENTS

| | | |
|---|---|---|
| 3,549,818 A | 12/1970 | Turner et al. |
| 3,585,416 A | 6/1971 | Mellen |
| 3,594,514 A | 7/1971 | Wingrove |
| 3,710,399 A | 1/1973 | Hurst |
| 3,712,962 A | 1/1973 | Epley |
| 3,764,748 A | 10/1973 | Branch et al. |
| 3,808,179 A | 4/1974 | Gaylord |
| 3,882,285 A | 5/1975 | Nunley et al. |
| 3,985,977 A | 10/1976 | Beaty et al. |
| 4,002,897 A | 1/1977 | Kleinman et al. |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,248,899 A | 2/1981 | Lyon et al. |
| 4,252,440 A | 2/1981 | Frosch et al. |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,339,954 A | 7/1982 | Anson et al. |
| 4,357,497 A | 11/1982 | Hochmair et al. |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,654,554 A | 3/1987 | Kishi |
| 4,689,819 A | 8/1987 | Killion |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Mariglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,425,104 A | 6/1995 | Shennib |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A | 7/1996 | Lesinski et al. |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,572,594 A | 11/1996 | Devoe et al. |
| 5,606,621 A | 2/1997 | Reiter et al. |
| 5,624,376 A | 4/1997 | Ball et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |
| 5,814,095 A | 9/1998 | Muller et al. |
| 5,825,122 A | 10/1998 | Givargizov et al. |
| 5,836,863 A | 11/1998 | Bushek et al. |
| 5,842,967 A | 12/1998 | Kroll |
| 5,851,199 A | 12/1998 | Peerless et al. |
| 5,857,958 A | 1/1999 | Ball et al. |
| 5,859,916 A | 1/1999 | Ball et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,017 A | 7/1999 | Bredberg et al. |
| 5,940,519 A | 8/1999 | Kuo |
| 5,949,895 A | 9/1999 | Ball et al. |
| 5,984,859 A | 11/1999 | Lesinski |
| 5,987,146 A | 11/1999 | Pluvinage et al. |
| 6,005,955 A | 12/1999 | Kroll et al. |
| 6,024,717 A | 2/2000 | Ball et al. |
| 6,045,528 A | 4/2000 | Arenberg et al. |
| 6,050,933 A | 4/2000 | Bushek et al. |
| 6,068,589 A | 5/2000 | Neukermans |
| 6,068,590 A | 5/2000 | Brisken |
| 6,084,975 A | 7/2000 | Perkins et al. |
| 6,093,144 A | 7/2000 | Jaeger et al. |
| 6,137,889 A | 10/2000 | Shennib et al. |
| 6,139,488 A | 10/2000 | Ball |
| 6,153,966 A | 11/2000 | Neukermans |
| 6,174,278 B1 | 1/2001 | Jaeger et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,217,508 B1 | 4/2001 | Ball et al. |
| 6,222,302 B1 | 4/2001 | Imada et al. |
| 6,222,927 B1 | 4/2001 | Feng et al. |
| 6,240,192 B1 | 5/2001 | Brennan et al. |
| 6,241,767 B1 | 6/2001 | Stennert et al. |
| 6,261,224 B1 | 7/2001 | Adams et al. |
| 6,277,148 B1 | 8/2001 | Dormer |
| 6,312,959 B1 | 11/2001 | Datskos |
| 6,339,648 B1 | 1/2002 | McIntosh et al. |
| 6,354,990 B1 | 3/2002 | Juneau et al. |
| 6,366,863 B1 | 4/2002 | Bye et al. |
| 6,385,363 B1 | 5/2002 | Rajic et al. |

(56) References Cited

U.S. PATENT DOCUMENTS

| | | |
|---|---|---|
| 6,387,039 B1 | 5/2002 | Moses |
| 6,393,130 B1 | 5/2002 | Stonikas et al. |
| 6,422,991 B1 | 7/2002 | Jaeger |
| 6,432,248 B1 | 8/2002 | Popp et al. |
| 6,436,028 B1 | 8/2002 | Dormer |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,644 B1 | 12/2002 | Vujanic et al. |
| 6,493,453 B1 | 12/2002 | Glendon |
| 6,493,454 B1 | 12/2002 | Loi et al. |
| 6,498,858 B2 | 12/2002 | Kates |
| 6,519,376 B2 | 2/2003 | Biagi et al. |
| 6,536,530 B2 | 3/2003 | Schultz et al. |
| 6,537,200 B2 | 3/2003 | Leysieffer et al. |
| 6,549,633 B1 | 4/2003 | Westermann |
| 6,554,761 B1 | 4/2003 | Puria et al. |
| 6,575,894 B2 | 6/2003 | Leysieffer et al. |
| 6,592,513 B1 | 7/2003 | Kroll et al. |
| 6,603,860 B1 | 8/2003 | Taenzer et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,668,062 B1 | 12/2003 | Luo et al. |
| 6,676,592 B2 | 1/2004 | Ball et al. |
| 6,695,943 B2 | 2/2004 | Juneau et al. |
| 6,724,902 B1 | 4/2004 | Shennib et al. |
| 6,728,024 B2 | 4/2004 | Ribak |
| 6,735,318 B2 | 5/2004 | Cho |
| 6,754,358 B1 | 6/2004 | Boesen et al. |
| 6,754,537 B1 | 6/2004 | Harrison et al. |
| 6,801,629 B2 | 10/2004 | Brimhall et al. |
| 6,829,363 B2 | 12/2004 | Sacha |
| 6,842,647 B1 | 1/2005 | Griffith et al. |
| 6,888,949 B1 | 5/2005 | Vanden Berghe et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,043,037 B2 | 5/2006 | Lichtblau |
| 7,050,675 B2 | 5/2006 | Zhou |
| 7,057,256 B2 | 6/2006 | Carey, III et al. |
| 7,058,182 B2 | 6/2006 | Kates |
| 7,072,475 B1 | 7/2006 | DeNap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,289,639 B2 | 10/2007 | Abel et al. |
| 7,322,930 B2 | 1/2008 | Jaeger et al. |
| 7,349,741 B2 | 3/2008 | Maltan et al. |
| 7,354,792 B2 | 4/2008 | Carey, III et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho et al. |
| 7,668,325 B2 | 2/2010 | Puria et al. |
| 7,867,160 B2 | 1/2011 | Pluvinage et al. |
| 7,983,435 B2* | 7/2011 | Moses ............ 381/326 |
| 8,401,214 B2 | 3/2013 | Perkins et al. |
| 2001/0003788 A1 | 6/2001 | Ball et al. |
| 2001/0027342 A1 | 10/2001 | Dormer |
| 2001/0043708 A1 | 11/2001 | Brimhall |
| 2001/0053871 A1 | 12/2001 | Zilberman et al. |
| 2002/0012438 A1 | 1/2002 | Leysieffer et al. |
| 2002/0029070 A1 | 3/2002 | Leysieffer et al. |
| 2002/0030871 A1 | 3/2002 | Anderson et al. |
| 2002/0035309 A1 | 3/2002 | Leysieffer |
| 2002/0086715 A1 | 7/2002 | Sahagen |
| 2002/0172350 A1 | 11/2002 | Edwards et al. |
| 2002/0183587 A1 | 12/2002 | Dormer |
| 2003/0064746 A1 | 4/2003 | Rader et al. |
| 2003/0097178 A1 | 5/2003 | Roberson et al. |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0220536 A1 | 11/2003 | Hissong |
| 2004/0165742 A1 | 8/2004 | Shennib et al. |
| 2004/0184732 A1 | 9/2004 | Zhou |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0240691 A1 | 12/2004 | Grafenberg |
| 2005/0020873 A1 | 1/2005 | Berrang et al. |
| 2005/0036639 A1 | 2/2005 | Bachler et al. |
| 2005/0163333 A1 | 7/2005 | Abel et al. |
| 2005/0226446 A1 | 10/2005 | Luo et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0107744 A1 | 5/2006 | Li et al. |
| 2006/0161255 A1 | 7/2006 | Zarowski et al. |
| 2006/0177079 A1 | 8/2006 | Baekgaard Jensen et al. |
| 2006/0183965 A1 | 8/2006 | Kasic, II et al. |
| 2006/0189841 A1* | 8/2006 | Pluvinage ............ 600/25 |
| 2006/0231914 A1 | 10/2006 | Carey, III et al. |
| 2006/0233398 A1 | 10/2006 | Husung |
| 2007/0083078 A1 | 4/2007 | Easter et al. |
| 2007/0100197 A1 | 5/2007 | Perkins et al. |
| 2007/0127748 A1 | 6/2007 | Carlile et al. |
| 2007/0135870 A1 | 6/2007 | Shanks et al. |
| 2007/0161848 A1 | 7/2007 | Dalton et al. |
| 2007/0191673 A1 | 8/2007 | Ball et al. |
| 2007/0225776 A1 | 9/2007 | Fritsch et al. |
| 2007/0236704 A1 | 10/2007 | Carr |
| 2007/0250119 A1 | 10/2007 | Tyler et al. |
| 2007/0251082 A1 | 11/2007 | Milojevic et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0107292 A1 | 5/2008 | Kornagel |
| 2008/0188707 A1 | 8/2008 | Bernard et al. |
| 2008/0298600 A1 | 12/2008 | Poe et al. |
| 2009/0023976 A1 | 1/2009 | Cho et al. |
| 2009/0043149 A1 | 2/2009 | Abel et al. |
| 2009/0092271 A1* | 4/2009 | Fay et al. ............ 381/328 |
| 2009/0097681 A1 | 4/2009 | Puria et al. |
| 2009/0141919 A1 | 6/2009 | Spitaels et al. |
| 2010/0034409 A1 | 2/2010 | Fay et al. |
| 2010/0048982 A1 | 2/2010 | Puria et al. |
| 2010/0145135 A1* | 6/2010 | Ball et al. ............ 600/25 |
| 2010/0312040 A1 | 12/2010 | Puria et al. |
| 2010/0317914 A1 | 12/2010 | Puria et al. |

FOREIGN PATENT DOCUMENTS

| | | |
|---|---|---|
| DE | 3508830 A1 | 9/1986 |
| EP | 0242038 A3 | 5/1987 |
| EP | 0242038 A2 | 10/1987 |
| EP | 0291325 A2 | 11/1988 |
| EP | 0296092 A2 | 12/1988 |
| EP | 0296092 A3 | 8/1989 |
| EP | 0352954 A2 | 1/1990 |
| EP | 0291325 A3 | 6/1990 |
| EP | 0352954 A3 | 8/1991 |
| EP | 1845919 A1 | 10/2007 |
| FR | 2455820 A1 | 11/1980 |
| JP | 60-154800 A | 8/1985 |
| JP | 09-327098 A | 12/1997 |
| KR | 10-0624445 B1 | 9/2006 |
| WO | WO 92/09181 A1 | 5/1992 |
| WO | WO 97/36457 A1 | 10/1997 |
| WO | WO 97/45074 A1 | 12/1997 |

(56) References Cited

FOREIGN PATENT DOCUMENTS

| WO | WO 98/06236 A1 | 2/1998 |
|---|---|---|
| WO | WO 99/03146 A1 | 1/1999 |
| WO | WO 99/15111 A1 | 4/1999 |
| WO | WO 00/22875 A2 | 4/2000 |
| WO | WO 00/22875 A3 | 7/2000 |
| WO | WO 01/50815 A1 | 7/2001 |
| WO | WO 01/58206 A2 | 8/2001 |
| WO | WO 01/58206 A3 | 2/2002 |
| WO | WO 02/39874 A2 | 5/2002 |
| WO | WO 02/39874 A3 | 2/2003 |
| WO | WO 03/063542 A2 | 7/2003 |
| WO | WO 03/063542 A3 | 1/2004 |
| WO | WO 2004/010733 A1 | 1/2004 |
| WO | WO 2005/015952 A1 | 2/2005 |
| WO | WO 2006/042298 A2 | 4/2006 |
| WO | WO 2006/075169 A1 | 7/2006 |
| WO | WO 2006/075175 A1 | 7/2006 |
| WO | WO 2006/042298 A3 | 10/2006 |
| WO | WO 2009/047370 A2 | 4/2009 |
| WO | WO 2009/056167 A1 | 5/2009 |
| WO | WO 2009/047370 A3 | 7/2009 |

OTHER PUBLICATIONS

U.S. Appl. No. 61/099,087, filed Sep. 22, 2008, Rucker.
Atasoy [Paper] Opto-acoustic Imaging. for BYM504E Biomedical Imaging Systems class at ITU, downloaded from the Internet www2.itu.edu.td-cilesiz/courses/BYM504- 2005-OA 504041413.pdf, 14 pages.
Athanassiou, et al. Laser controlled photomechanical actuation of photochromic polymers Microsystems. Rev. Adv. Mater. Sci. 2003; 5:245-251.
Ayatollahi, et al. Design and Modeling of Micromachined Condenser MEMS Loudspeaker using Permanent Magnet Neodymium—Iron—Boron (Nd—Fe—B). IEEE International Conference on Semiconductor Electronics, 2006. ICSE '06, Oct. 29, 2006-Dec. 1 2006; 160-166.
Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.
Best, et al. The influence of high frequencies on speech localization. Abstract 981 (Feb. 24, 2003) from www.aro.org/abstracts/abstracts.html.
Birch, et al. Microengineered systems for the hearing impaired. IEE Colloquium on Medical Applications of Microengineering, Jan. 31, 1996; pp. 2/1-2/5.
Burkhard, et al. Anthropometric Manikin for Acoustic Research. J. Acoust. Soc. Am., vol. 58, No. 1, (Jul. 1975), pp. 214-222.
Camacho-Lopez, et al. Fast Liquid Crystal Elastomer Swims Into the Dark, Electronic Liquid Crystal Communications. Nov. 26, 2003; 9 pages total.
Carlile, et al. Spatialisation of talkers and the segregation of concurrent speech. Abstract 1264 (Feb. 24, 2004) from www.aro.org/abstracts/abstracts.html.
Cheng, et al. A Silicon Microspeaker for Hearing Instruments. Journal of Micromechanics and Microengineering 2004; 14(7):859-866.
Datskos, et al. Photoinduced and thermal stress in silicon microcantilevers. Applied Physics Letters. Oct. 19, 1998; 73(16):2319-2321.
Decraemer, et al. A method for determining three-dimensional vibration in the ear. Hearing Res., 77:19-37 (1994).
Fay, et al. Cat eardrum response mechanics. Calladine Festschrift (2002), Ed. S. Pellegrino, The Netherlands, Kluwer Academic Publishers.
Fay. Cat eardrum mechanics. Ph.D. thesis. Dissertation submitted to Department of Aeronautics and Astronautics. Standford University. May 2001; 210 pages total.
Fletcher. Effects of Distortion on the Individual Speech Sounds. Chapter 18, ASA Edition of Speech and Hearing in Communication, Acoust Soc.of Am. (republished in 1995) pp. 415-423.

Freyman, et al. Spatial Release from Informational Masking in Speech Recognition. J. Acost. Soc. Am., vol. 109, No. 5, pt. 1, (May 2001); 2112-2122.
Freyman, et al. The Role of Perceived Spatial Separation in the Unmasking of Speech. J. Acoust. Soc. Am., vol. 106, No. 6, (Dec. 1999); 3578-3588.
Gennum, GA3280 Preliminary Data Sheet: Voyageur TD Open Platform DSP System for Ultra Low Audio Processing, downloaded from the Internet: www.sounddesigntechnologies.com/products/pdf/37601DOC.pdf, Oct. 2006; 17 pages.
Gobin, et al. Comments on the physical basis of the active materials concept. Proc. SPIE 2003; 4512:84-92.
Hato, et al. Three-dimensional stapes footplate motion in human temporal bones. Audiol. Neurootol., 8:140-152 (Jan. 30, 2003).
Hofman, et al. Relearning Sound Localization With New Ears. Nature Neuroscience, vol. 1, No. 5, (Sep. 1998); 417-421.
International search report and written opinion dated Jan. 18, 2011 for PCT/US2010/039240.
Izzo, et al. Laser Stimulation of Auditory Neurons: Effect of Shorter Pulse Duration and Penetration Depth. Biophys J. Apr. 15, 2008;94(8):3159-3166.
Izzo, et al. Laser Stimulation of the Auditory Nerve. Lasers Surg Med. Sep. 2006;38(8):745-753.
Izzo, et al. Selectivity of Neural Stimulation in the Auditory System: A Comparison of Optic and Electric Stimuli. J Biomed Opt. Mar.-Apr. 2007;12(2):021008.
Jin, et al. Speech Localization. J. Audio Eng. Soc. convention paper, presented at the AES 112th Convention, Munich, Germany, May 10-13, 2002, 13 pages total.
Killion. Myths About Hearing Noise and Directional Microphones. The Hearing Review. Feb. 2004; 11(2):14, 16, 18, 19, 72 & 73.
Killion. SNR loss: I can hear what people say but I can't understand them. The Hearing Review, 1997; 4(12):8-14.
Lee, et al. The optimal magnetic force for a novel actuator coupled to the tympanic membrane: a finite element analysis. Biomedical engineering: applications, basis and communications. 2007; 19(3):171-177.
Lezal. Chalcogenide glasses—survey and progress. J. Optoelectron Adv Mater., Mar. 2003; 5 (1):23-34.
Markoff. Intuition + Money: An Aha Moment. New York Times Oct. 11, 2008, p. BU4, 3 pages total.
Martin, et al. Utility of Monaural Spectral Cues is Enhanced in the Presence of Cues to Sound-Source Lateral Angle. JARO. 2004; 5:80-89.
Moore. Loudness perception and intensity resolution. Cochlear Hearing Loss, Chapter 4, pp. 90-115, Whurr Publishers Ltd., London (1998).
Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.
Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.
National Semiconductor, LM4673 Boomer: Filterless, 2.65W, Mono, Class D Audio Power Amplifier, [Data Sheet] downloaded from the Internet: <<http://www.national.com/ds/LM/LM4673.pdf>>; Nov. 1, 2007; 24 pages.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
Perkins, et al. The EarLens System: New sound transduction methods. Hear Res. Feb. 2, 2010; 10 pages total.
Poosanaas, et al. Influence of sample thickness on the performance of photostrictive ceramics, J. App. Phys. Aug. 1, 1998; 84(3):1508-1512.
Puria et al. A gear in the middle ear. ARO Denver CO, 2007b.
Puria, et al. Malleus-to-footplate ossicular reconstruction prosthesis positioning: cochleovestibular pressure optimization. Otol Nerotol. May 2005; 26930:368-379.
Puria, et al. Measurements and model of the cat middle ear: Evidence of tympanic membrane acoustic delay. J. Acoust. Soc. Am., 104(6):3463-3481 (Dec. 1998).

(56) References Cited

OTHER PUBLICATIONS

Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.

Puria, et al. Sound-Pressure Measurements in the Cochlear Vestibule of Human-Cadaver Ears. Journal of the Acoustical Society of America. 1997; 101 (5-1): 2754-2770.

Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light-material-could-upend-solar-imaging-industries> 4 pages total.

Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.

Sekaric, et al. Nanomechanical resonant structures as tunable passive modulators. App. Phys. Left. Nov. 2003; 80(19):3617-3619.

Shaw. Transformation of Sound Pressure Level From the Free Field to the Eardrum in the Horizontal Plane. J. Acoust. Soc. Am., vol. 56, No. 6, (Dec. 1974), 1848-1861.

Shih. Shape and displacement control of beams with various boundary conditions via photostrictive optical actuators. Proc. IMECE. Nov. 2003; 1-10.

Sound Design Technologies,—Voyager TDTM Open Platform DSP System for Ultra Low Power Audio Processing—GA3280 Data Sheet. Oct. 2007; retrieved from the Internet: www.sounddes.com/pdf/37601DOC.pdf, 15 page total.

Stenfelt, et al. Bone-Conducted Sound: Physiological and Clinical Aspects. Otology & Neurotology, Nov. 2005; 26 (6):1245-1261.

Stuchlik, et al. Micro-Nano Actuators Driven by Polarized Light. IEEE Proc. Sci. Meas. Techn. Mar. 2004; 151(2):131-136.

Stuchlik, et al. Micro-Nano actuators driven by polarized light. IEE Proc. Sci. Meas. Techn. Mar. 2004; 151(2):131-136.

Suski, et al. Optically activated ZnO/Si02/Si cantilever beams. Sensors and Actuators A (Physical), 0 (nr: 24). 2003; 221-225.

Takagi, et al. Mechanochemical Synthesis of Piezoelectric PLZT Powder. KONA. 2003; 51(21):234-241.

Thakoor, et al. Optical microactuation in piezoceramics. Proc. SPIE. Jul. 1998; 3328:376-391.

Tzou, et al. Smart Materials, Precision Sensors/Actuators, Smart Structures, and Structronic Systems. Mechanics of Advanced Materials and Structures. 2004; 11:367-393.

Uchino, et al. Photostricitve actuators. Ferroelectrics. 2001; 258:147-158.

Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.

Vinikman-Pinhasi, et al. Piezoelectric and Piezooptic Effects in Porous Silicon. Applied Physics Letters, Mar. 2006; 88(11): 11905-111906.

Wang, et al. Preliminary assessment of remote photoelectric excitation of an actuator for a hearing omplant. Proceeding of the 2005 IEEE, Engineering in Medicine and Biology 27th annual conference, Shanghai, China. Sep. 1-4, 2005; 6233-6234.

Wiener, et al. On the Sound Pressure Transformation by the Head and Auditory Meatus of the Cat. Acta Otolaryngol. Mar. 2006; 61(3):255-269.

Wightman, et al. Monaural Sound Localization Revisited. J. Acoust. Soc. Am. Feb. 1997; 101(2):1050-1063.

Yu et al. Piezoelectric Microspeaker with Compressive Nitride Diaphragm. The Fifteenth IEEE International Conference on Micro Electro Mechanical Systems, 2002; 260-263.

Yu, et al. Photomechanics: Directed bending of a polymer film by light. Nature. Sep. 2003; 425:145.

European search report and search opinion dated Nov. 5, 2013 for EP Application No. 10790292.

* cited by examiner

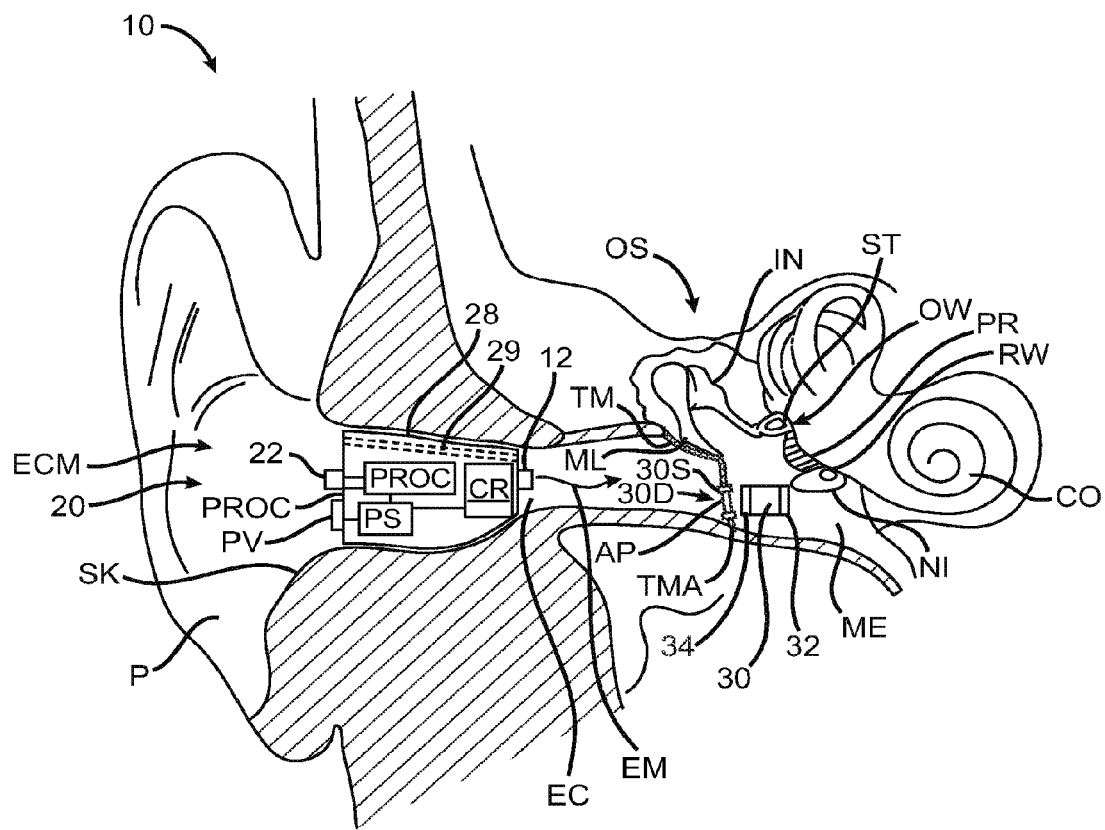
FIG. 1A1

FIG. 1B  FIG. 1B1  FIG. 1B2

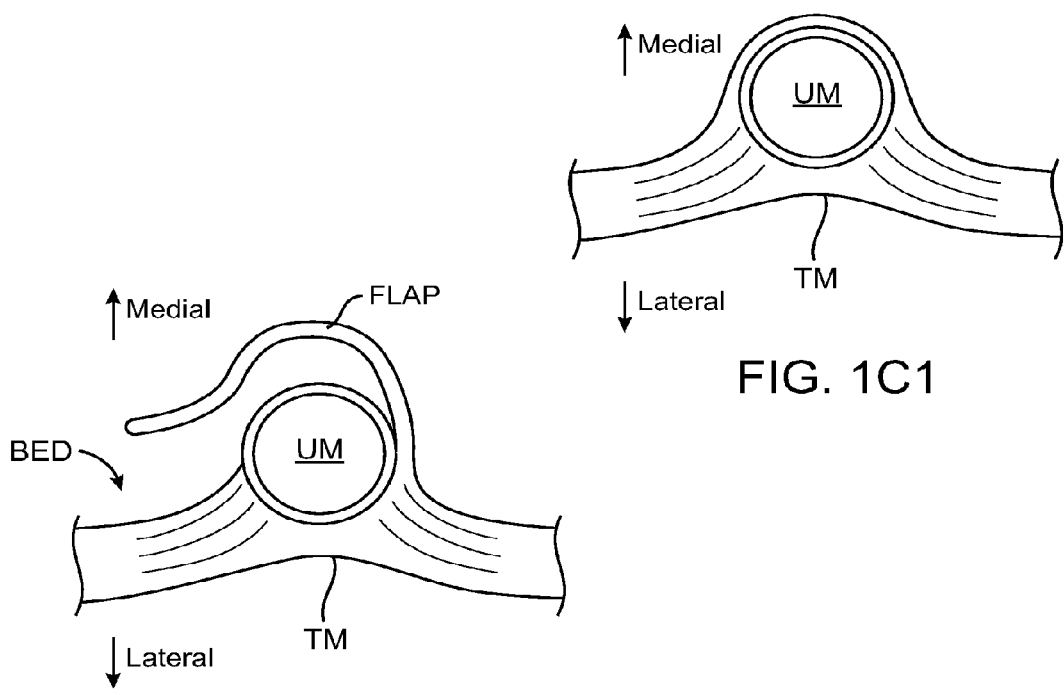
FIG. 1C1
FIG. 1C2
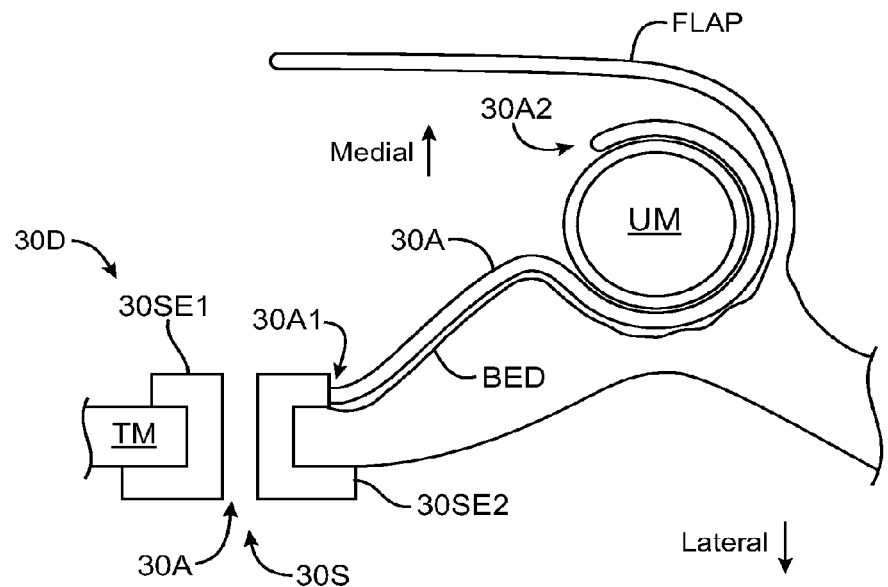
FIG. 1C3

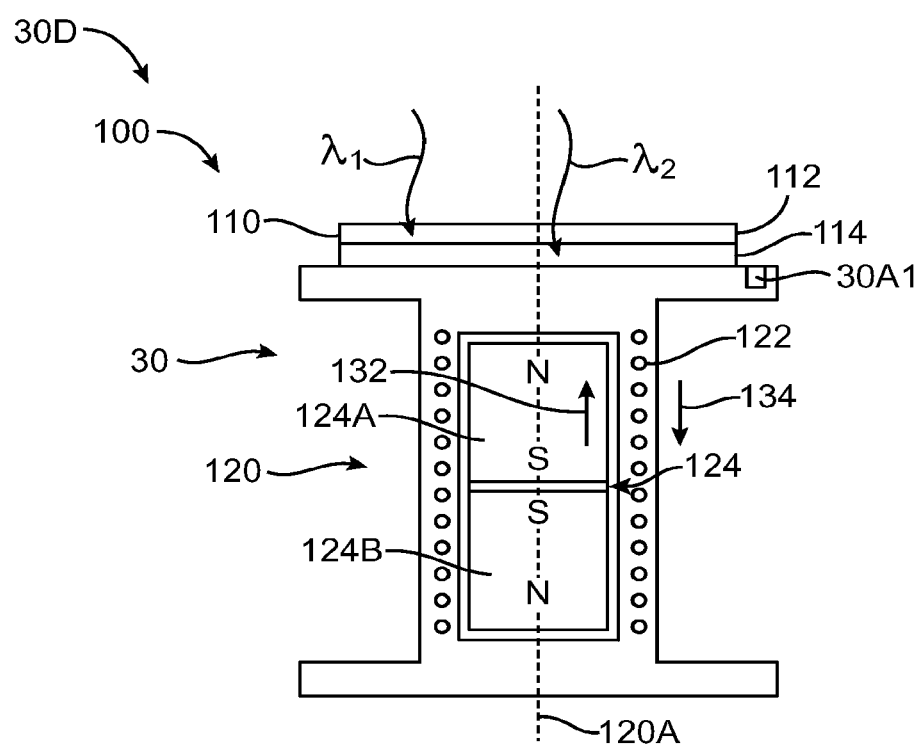
FIG. 2B1

EARDRUM IMPLANTABLE DEVICES FOR HEARING SYSTEMS AND METHODS

CROSS REFERENCE TO RELATED APPLICATIONS

The present application is a divisional of U.S. application Ser. No. 12/818,449 filed Jun. 18, 2010, now U.S. Pat. No. 8,401,214, issued Mar. 19, 2013, which is a non-provisional of U.S. Appl. Ser. No. 61/218,380 filed on 18 Jun. 2009, entitled "Eardrum Implantable Devices for Hearing Systems and Methods" the full disclosure of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Field of the Invention

The present invention is related to hearing systems, devices and methods. Although specific reference is made to hearing aid systems, embodiments of the present invention can be used in many applications in which a signal is used to stimulate the ear.

People like to hear. Hearing allows people to listen to and understand others. Natural hearing can include spatial cues that allow a user to hear a speaker, even when background noise is present. People also like to communicate with those who are far away, such as with cellular phones.

Hearing devices can be used with communication systems to help the hearing impaired and to help people communicate with others who are far away. Hearing impaired subjects need hearing aids to verbally communicate with those around them. Open canal hearing aids have proven to be successful in the marketplace because of increased comfort and an improved cosmetic appearance. Another reason why open canal hearing aides can be popular is reduced occlusion of the ear canal. Occlusion can result in an unnatural, tunnel-like hearing effect which can be caused by large hearing aids which block the ear canal. In at least some instances, occlusion can be noticed by the user when he or she speaks and the occlusion results in an unnatural sound during speech. However, a problem that may occur with open canal hearing aids is feedback. The feedback may result from placement of the microphone in too close proximity with the speaker or the amplified sound being too great. Thus, feedback can limit the degree of sound amplification that a hearing aid can provide. Although feedback can be minimized by placing the microphone outside the ear canal, this placement can result in the device providing an unnatural sound that is devoid of the spatial location information cues present with natural hearing.

In some instances, feedback may be decreased by using non-acoustic means of stimulating the natural hearing transduction pathway, for example stimulating the tympanic membrane, bones of the ossicular chain and/or the cochlea. An output transducer may be placed on the eardrum, the ossicles in the middle ear, or the cochlea to stimulate the hearing pathway. However, surgery may be needed to place a hearing device on the ossicles or cochlea, and such surgery can involve delicate and complex movements to position the implant and can be somewhat invasive, for example with the cutting and drilling of bone, in at least some instances. The cutting and/or drilling of bone can delay healing and recovery time, such that implantation of at least some of the prior devices in the middle ear may not be well suited for at least some patients in at least some instances. At least some of the prior implants located on the ossicles or the cochlea can result in occlusion in at least some instances, and distortion of the sound can be perceptible in at least some instances.

One promising approach has been to place a magnet on the eardrum and drive the magnet with a coil positioned away from the eardrum. The magnet can be electromagnetically driven with a coil to cause motion in the hearing transduction pathway thereby causing neural impulses leading to the sensation of hearing. A permanent magnet may be coupled to the ear drum through the use of a fluid and surface tension, for example as described in U.S. Pat. Nos. 5,259,032 and 6,084,975. Although this approach can result in decreased feedback and shows promise, there is still room for improvement. The magnet may be positioned on the eardrum with a support and a coupling liquid such as an oil, and work in relation to embodiments of the present invention suggests that in at least some instances the user may need to place drops in the ear for the magnet and support to remain coupled to the eardrum, such that in at least some instances the support can decouple from the eardrum. Also, in at least some instances, a magnet positioned on the ear may be sensitive to external electromagnetic fields that can result in a perceptible noise, for example a humming sound in at least some instances.

Another promising approach has been to optically couple a hearing device, such that noise from electromagnetic interference can be decreased. However, in at least some instances the prior systems that transmit light to a transducer can result in perceptible noise and distortion in the optically transmitted signal, such that the sound quality of such devices can be less than ideal in at least some instances. For example, at least some optical systems may comprise non-linearity that can distort the signal and may result in user-perceptible distortion in at least some instances. Work in relation to embodiments of the present invention also suggests that light transmission through the eardrum to the photodetector may contribute to distortion in at least some instances.

For the above reasons, it would be desirable to provide hearing systems which at least decrease, or even avoid, at least some of the above mentioned limitations of the prior hearing devices. For example, there is a need to provide a comfortable hearing device which provides hearing with natural qualities, for example with spatial information cues, and which allow the user to hear with less occlusion, distortion and feedback than prior devices.

BRIEF SUMMARY OF THE INVENTION

Embodiments of the present invention provide improved hearing devices, systems and methods that overcome at least some of the above identified limitations of the prior devices. An implantable device is configured for placement in the eardrum to transmit an audio signal to a user. The device can be configured in many ways to transmit the audio signal to the user. For example, the device may be configured to improve transmission of an electromagnetic signal comprising light energy from an input assembly on a lateral side of eardrum to an output assembly positioned on a medial side of the eardrum, for example at least partially in the middle ear of the user. The output assembly may comprise a transducer or at least two electrodes configured to stimulate the cochlea, for example. The device may comprise an opening to transmit the light signal or an optic to transmit the light signal. Alternatively the device may be configured to support a transducer of the output assembly with the eardrum when the device is implanted in the eardrum, such that the eardrum vibrates in response to the signal electromagnetic signal. The signal may comprise a magnetic field from a coil positioned in the ear canal and the transducer supported with the implanted device may comprise a magnet.

Alternatively, the electromagnetic signal may comprise light energy. The device may comprise photodetector configured to vibrate the assembly in response to the light energy.

In a first aspect, embodiments of the present invention provide an apparatus to transmit sound to a user having an eardrum. At least one light source is configured to generate light energy. At least one photodetector is sensitive to the light energy and configured for placement in the middle ear. An implantable device comprising a structure is configured for placement at least partially in the eardrum, in which the implantable device is configured to transmit the light energy from the at least one light source to the photodetector.

In many embodiments, the eardrum implantable device comprises an opening configured to transmit the light energy.

In many embodiments, the eardrum implantable device may comprise a light transmitting material configured to transmit the light energy. The eardrum implantable device may comprise an optic configured to transmit the light energy. The optic may comprise at least one of a converging lens, a diverging lens, a diffractive optic, a Fresnel lens, a light diffusing optic, a prism, or a transparent window. The optically transparent material comprises a molded biocompatible material.

In many embodiments, the eardrum implantable device comprises a single piece composed of a molded light transmitting material.

In many embodiments, the structure comprises a first flange on a first side and a second flange on a second side, the first flange disposed opposite the second flange. The first flange can be separated from the second flange by a separation distance sized to receive a portion of the eardrum. The first flange may comprise a first maximum distance across and the second flange may comprise a second maximum across, and the second distance across can be less than the first distance across such that the second flange is sized to pass through a hole in the eardrum and the first flange is sized to contact tissue that defines the hole in the eardrum.

In many embodiments, an anchor is configured to extend from the structure to an umbo of the eardrum to anchor the structure to the eardrum. The anchor can be configured to disconnect from the umbo when the structure is removed from the eardrum. The anchor may comprise an elongate flexible structure configured to extend at least partially around the umbo. For example, the anchor may comprise a hook sized to extend at least partially around the umbo.

In many embodiments, the structure is configured to couple to the anchor with a distal portion of the structure. For example, the distal portion of the structure may comprise a flange, and the flange may comprise a hole sized to receive the anchor.

In many embodiments, the anchor is affixed to the flange.

In many embodiments, an input assembly comprising the at least one light source configured for placement and an output assembly comprising the at least one photodetector, the input transducer assembly configured for placement at least partially within an ear canal or behind a pinna of the user, the output assembly configured for placement in a middle ear of the user to couple the output assembly with the input assembly.

In another aspect, embodiments of the present invention provide a device to transmit a sound to a user having an eardrum. A structure is configured for placement in the eardrum, and a transducer is supported with the structure and configured to vibrate the eardrum.

In many embodiments, the transducer comprises at least one of a magnet, a coil, a coil and magnet transducer, a piezoelectric transducer, a balanced armature transducer, a photostrictive transducer or a magnetostrictive transducer. For example, the transducer may comprise the magnet, and the magnet is affixed to the structure to vibrate the eardrum in response to a coil positioned in an ear canal of the user.

In many embodiments, at least one of a coil or at least one photodetector is supported with the structure and coupled to the transducer, and the at least one of the coil or the at least one photodetector is configured to receive electromagnetic energy and vibrate the transducer in response to the audio signal such that the user perceives the sound.

In many embodiments, the transducer comprises a pair of opposing magnets disposed within the coil so as to vibrate the eardrum in response to the audio signal.

In many embodiments, an anchor configured to anchor the structure to the eardrum.

In another aspect, embodiments of the present invention provide a method of transmitting a sound to a user. Light energy is transmitted to a device comprising a structure placed at least partially in an eardrum of the user.

In many embodiments, the light energy is transmitted through the device to a photodetector positioned medial of the structure.

In many embodiments, a transducer is supported with the structure and the transducer vibrates such that the user perceives the sound.

In another aspect, embodiments of the present invention provide a method of providing hearing to a user having an eardrum. A hearing device configured for placement in the eardrum is provided, and the hearing device is placed at least partially in the eardrum.

In many embodiments, at least one photodetector is positioned in a middle ear of the user and the structure is configured to transmit light.

In many embodiments, the structure is configured to support a transducer configured to vibrate the eardrum.

In many embodiments, an anchor is attached to a malleus of the user to anchor the structure in the eardrum. The anchor can be coupled to the structure on a medial side of the structure. The eardrum can be cut to form a flap on a medial side of the eardrum, and the flap can be positioned at least partially over the anchor when the anchor is attached to the malleus. The structure can be positioned in an at least partially inferior and at least partially anterior portion of the eardrum.

BRIEF DESCRIPTION OF THE DRAWINGS

FIG. 1A1 shows an optically coupled system comprising an ear canal module, in accordance with embodiments;

FIG. 1B shows an implantable device comprising a structure to retain the device in the eardrum and an aperture configured for use with a system as in FIGS. 1A and 1A1;

FIG. 1B1 shows an optic suitable for placement in the aperture as in FIG. 1B;

FIG. 1B2 shows an implantable device comprising a light transmitting material configured for placement in an eardrum of a user, in accordance with embodiments;

FIG. 1C1 shows a malleus of a user connected to an eardrum TM at an umbo suitable for connection with an anchor, in accordance with embodiments;

FIG. 1C2 shows an eardrum and a malleus as in FIG. 1C1 in which a flap of tissue has been formed with an incision in the eardrum TM;

FIG. 1C3 shows an anchor connected to the umbo and the implantable device such that the a flap as in FIG. 1C2 is configured for placement over the anchor;

FIG. 2B1 shows the assembly and the transducer, in which the magnet comprises a pair of opposing magnets, in accordance with embodiments.

DETAILED DESCRIPTION OF THE INVENTION

As used herein light encompasses infrared light, visible light and ultraviolet light.

Figure 1A:
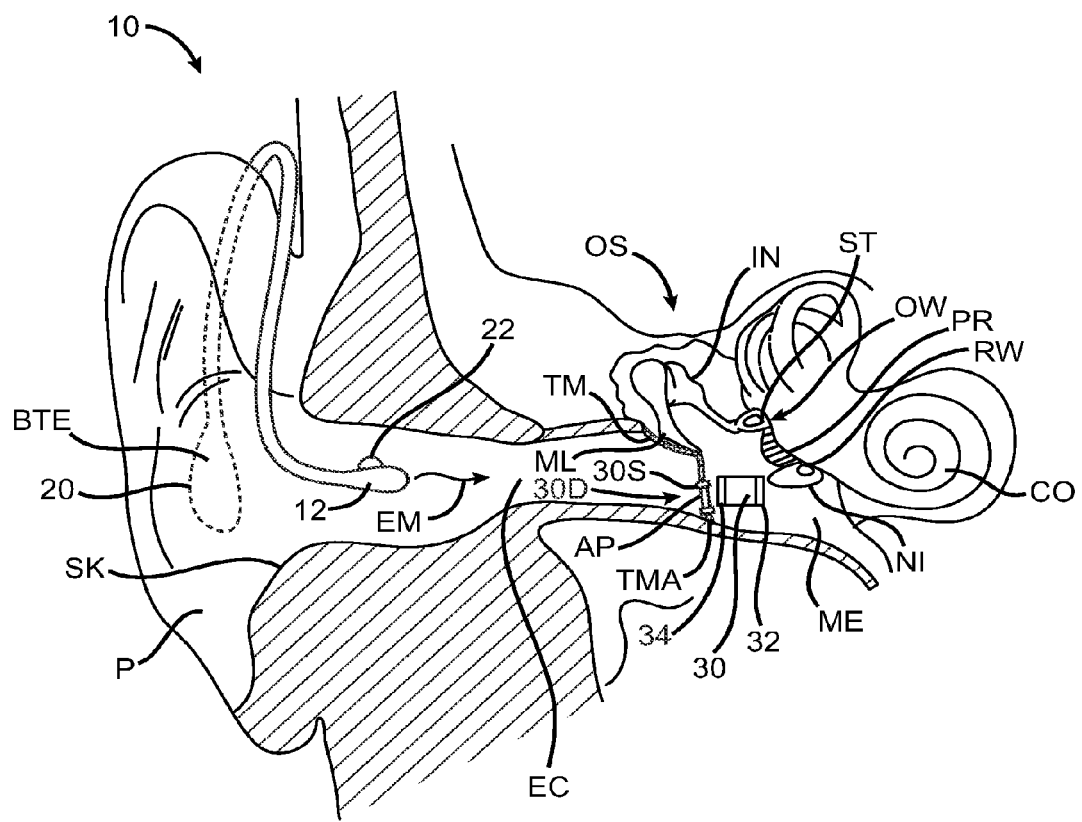
FIG. 1A shows an optically coupled implant system comprising an input assembly, an output assembly, and an eardrum implantable device comprising a retention structure implanted in the eardrum of the user, in accordance with embodiments.

FIG. 1A shows an optically coupled implant system 10 comprising an input assembly 20 and an output assembly 30, and an eardrum implantable device 30D implanted in the eardrum of the user. The eardrum implantable device 30D comprises a retention structure 30S to retain the eardrum implantable device in the eardrum TM of the user. The input assembly 20 may comprise behind the ear unit (hereinafter "BTE"). The BTE unit can be positioned behind a pinna P of the user, so as to decrease visibility of the BTE unit. The BTE unit can house electronics used to process and input signal. An input transducer of inputs assembly 10, for example microphone 22, is coupled to the BTE unit and can transmit an audio signal to the BTE unit. The BTE can convert the input signal into an electromagnetic signal EM. The electromagnetic signal may comprise an optical signal produced by at least one optical source such as a laser, or an electromagnetic signal from a coil. For example a support can extend into the ear canal and support a coil as described in as described in U.S. application Ser. No. 12/244,266, entitled, "Energy Delivery and Microphone Placement Methods for Improved Comfort in an Open Canal Hearing Aid", filed Oct. 2, 2008, the full disclosure of which is incorporated herein by reference and may be suitable for combination in accordance with embodiments of the present invention. Alternatively, the BTE unit can be coupled to an optical transmission structure 12 to emit an electromagnetic signal EM comprising the optical signal $\lambda_S$. The light transmission structure 12 can extend from the BTE into the ear canal EC. The light transmission structure 12 may support microphone 22.

The input of input assembly 20 can come from many sources such as a microphone, a second microphone, or a radio coupled to an electronics devices such as a cell phone, computer, etc. Microphone 22 can be positioned in many locations, for example within the ear canal or near the ear canal opening to detect sound localization cues. The input transducer may comprise a second microphone positioned on the BTE unit for noise cancelation. The sound input to the assembly may comprise sound from a Bluetooth connection, and the BTE may comprise circuitry to couple with a cell phone, for example. For example, the input transducer assembly may be located substantially within the ear canal, as described in U.S. Pub. No. 2006/0251278, the full disclosure of which is incorporated by reference. The input transducer assembly may comprise a blue tooth connection to couple to a cell phone and my comprise, for example, components of the commercially available Sound ID 300, available from Sound ID of Palo Alto, Calif.

The output assembly 30 is configured for placement at least partially in the middle ear of the user and in some embodiments may extend into the inner ear, for example with cochlear implants. The output assembly 30 comprises at least one detector 34 configured to receive the optical signal $\lambda_S$. The output assembly comprise may comprise an output transducer or at least two electrodes coupled to the at least one detector 34 so as to stimulate tissue, such as with vibration of the transducer or with electrical current to stimulate the cochlea in response to the optical signal $\lambda_S$. The output assembly 30 may comprise many kinds of transducers to vibrate the auditory system such that the user perceives sound. For example, the transducer may comprise at least one of a magnet, a coil, a coil and magnet transducer, a piezoelectric transducer, a balanced armature transducer, a photostrictive transducer or a magnetostrictive transducer Alternatively, the at least one photodetector can be coupled to at least two electrodes, for example of an electrode array, so as to couple the at least one photodetector to the at least two electrodes.

The hearing system 10 can leave the natural hearing pathway of the user substantially function and intact with decreased interference from the system 10. Skin SK of the external ear can support the input assembly. The Pinna P can focus sound toward the ear canal EC, such that sound localization cues can be detected by microphone 22. The eardrum TM is coupled to ossicles OS so as to conduct sound to the cochlea CO where vibrations are sensed by the user as sound. The ossicles comprise a malleus ML, an incus IN and a stapes ST. The stapes ST couples to the cochlea with an oval window OW. The round window can be disposed along a channel of the cochlea opposite the oval window OW such that the round window RW vibrates in response to sound. The round window may be located in a round window niche NI. The eardrum TM may comprise an annulus TMA. An incision may be formed in the eardrum TM and optionally in the annulus TMA to insert components the output assembly in the middle ear ME.

FIG. 1A1 shows an input assembly 20 of system 10 comprising an ear canal module (hereinafter "ECM"). The ECM may comprise many of the components of the BTE unit and vice-versa. The ECM may be shaped from a mold of the user's ear canal EC. Circuitry CR can be coupled to microphone 22. The circuitry may comprise a sound processor. The ECM may comprise an energy storage device PS configured to store electrical energy. The storage device may comprise many known storage devices such at least one of a battery, a rechargeable battery, a capacitor, a supercapacitor, or electrochemical double layer capacitor (EDLC). The ECM can be removed, for example for recharging or when the user sleeps. The ECM may comprise a channel 29 to pass air so as to decrease occlusion. Although air is passed through channel 29, feedback can be decrease due to coupling of the transducer or electrode array directly to tissue.

The energy storage device PS may comprise a rechargeable energy storage device that can be recharged in many ways. For example, the energy storage device may be charged with a plug in connector coupled to a super capacitor for rapid charging. Alternatively, the energy storage device may be charged with an inductive coil or with a photodetector PV. The photodetector detector PV may be positioned on a proximal end of the ECM such that the photodetector is exposed to light entering the ear canal EC. The photodetector PV can be coupled to the energy storage device PS so as to charge the energy storage device PS. The photodetector may comprise many detectors, for example black silicone as described above. The rechargeable energy storage device can be provided merely for convenience, as the energy storage device PS may comprise batteries that the user can replace when the ECM is removed from ear canal.

The photodetector PV may comprise at least one photovoltaic material such as crystalline silicon, amorphous silicon, micromorphous silicon, black silicon, cadmium telluride, copper indium gallium selenide, and the like. In some embodiments, the photodetector PV may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications Nos. 61/073,271, entitled "Optical Electro-Mechanical Hearing Devices With Combined Power and Signal Architectures"; and 61/073,281, entitled "Optical Electro-Mechanical Hearing Devices with Separate Power and Signal", the full disclosures of which have been previously incorporated herein by reference and may be suitable for combination in accordance with some embodiments as described herein.

The BTE may comprise many of the components of the ECM, for example photodetector PV, energy storage device PS, the processor and circuitry, as described above.

FIG. 1B shows the eardrum implantable device 30D comprising the structure 30S to retain the device in the eardrum TM. The eardrum implantable device can be configured for use with a system as in FIGS. 1A and 1A1. The eardrum implantable device 30D may comprise an aperture 30SAP. Alternatively or in combination, the eardrum implantable device may comprise an optic, a light transmitting material, a transducer, or many combinations thereof. The eardrum implantable device may be composed of many biocompatible materials. For example, device 30D may comprise a soft and flexible material so as to inhibit irritation to the eardrum TM. The device 30TM may comprise a single piece of a molded material. For example, device 30D may comprise a single piece of molded biocompatible silicone elastomer material. The biocompatible material may comprise a light transmitting material, for example a transparent light transmitting material.

The retention structure 30S can be configured in many ways to retain the device in the eardrum TM. For example, the retention structure 30S may comprise a first extension 30SE1, such as a first annular flange, and a second extension 30SE2 such as a second annular flange. Many additional or alternative extensions can be used such as radially extending spokes, rings and spirals, for example. The first extension and the second extension can be separated by an separation distance sized to a thickness of the eardrum TM, such that the retention structure is sized to receive the eardrum TM between the first extension and the second extension. The first extension 30SE1 may correspond to a distal end of the device, and the second extension 30SE2 may comprise a proximal end of the device. The first extension 30SE1 may comprise a maximum distance across, for example a diameter, and the second extension 30SE2 may comprise a maximum distance across, for example a diameter. The first distance across the distal end may be smaller than the second distance across the proximal end such that the first end is sized to pass through an opening in eardrum TM. The aperture 30SAP may comprise a cylindrical shape defined by an annular portions of device 30S. For example, device 30S may comprise a fir FIG. 1B1 shows an optic suitable for placement in the aperture as in FIG. 1B. The optic may comprise a size similar to the aperture AP, such that the optic can be placed in the aperture during assembly. The optic may comprise at least one of a converging lens, a diverging lens, a diffractive optic, a Fresnel lens, a light diffusing optic, a prism, or a transparent window. The optic can be configured to transmit light energy from a source lateral to the eardrum TM to at least one detector positioned medial to the eardrum TM. For example, the optic may comprise a diffuse configured to spread light energy, such that light energy coupling from the source to the at least one detector remains substantially constant when the eardrum moves, for example vibrates in response to sound. The optic may comprise a window, for example such that light can be passed from the source to the detector so as to retain properties of the transmitted light, for example coherence of the light signal.

FIG. 1B2 shows the implantable device 30D comprising a light transmitting material 30STR configured for placement in an eardrum of a user. The light transmitting material may comprise a non-transparent scattering material, for example. Alternatively or in combination, the light transmitting material 30STR may comprise a transparent material with a smooth surface on the first and second ends such that the transparent material comprises a window. The implantable device 30D comprising the light transmitting material 30STR may comprise a single piece of molded light transmitting material.

Figure 1C:
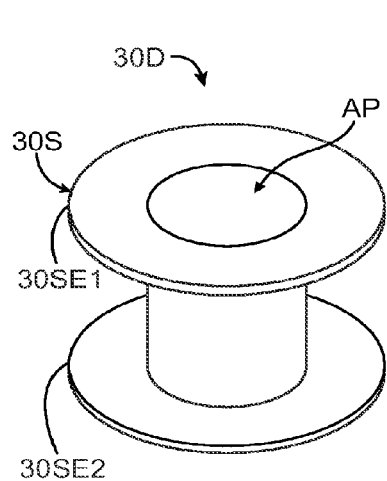
FIG. 1C shows an implantable device positioned in an eardrum of a user, in accordance with embodiments.
Figure 1C:
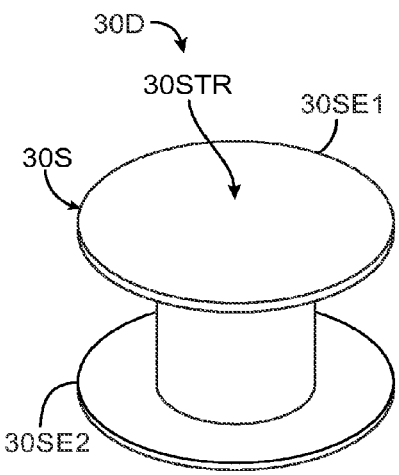
Figure 1C:
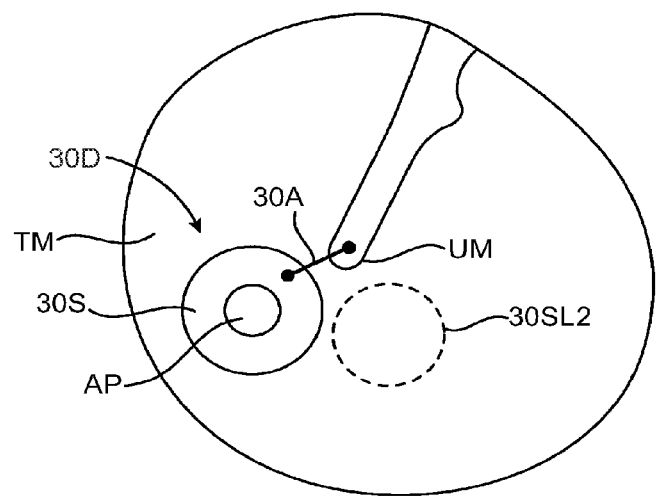

FIG. 1C shows implantable device 30D positioned in an eardrum of a user. Device 30D can be positioned in many locations in the eardrum TM of the user. Work in relation with embodiments suggests that placement in an anterior-inferior location of the eardrum can decrease migration of the implanted device, which may be related to centripetal migration of the epithelium away from an inner location of the eardrum toward an outer location of the eardrum. The amount of migration of an eardrum implant can be related to duration of the implant in eardrum and location.

Work in relation to embodiments suggests that an anchor 30A may be helpful to retain the implantable device 30D at an intended location in the eardrum TM. A person of ordinary skill in the art can conduct experiments, based on the teachings described herein, to determine whether an anchor is helpful.

The anchor 30A may be connected to the implant and the malleus ML, for example at the umbo UM of the malleus. As the malleus connects with the eardrum at the umbo, the tissue connecting the malleus to the umbo can provide a suitable location to connect the anchor to the malleus.

The device 30D can be implanted at many locations of the eardrum. For example the device 30D may be implanted at an alternative location 30SL2, located inferior to the umbo UM, and held in place with the anchor 30A.

FIG. 1C1 shows a malleus of a user connected to an eardrum TM at an umbo suitable for connection with an anchor. The eardrum TM comprise a greater thickness at the umbo UM than at peripheral portions of the eardrum TM. The anchor may be coupled to the umbo UM with medial access, such that the eardrum can substantially retain barrier and protective function so as to protect the middle ear and inner ear.

FIG. 1C2 shows an eardrum and a malleus as in FIG. 1C1 in which a flap of tissue has been formed with an incision in the eardrum TM. The flap can be separated from a bed of tissue such that the lateral side of the eardrum extending from the umbo to the implantable device 30D remains intact. The flap of tissue can be at least partially resected from eardrum TM with an incision near the umbo. The flap may remain connected to the eardrum TM when the anchor is positioned so as to facilitate repositioning of the flap from the bed where the flap has been removed. The flap may be removed medially.

FIG. 1C3 shows an anchor connected to the umbo and the implantable device such that the flap as in FIG. 1C2 is configured for placement over the anchor. The anchor may extend at least partially around the umbo so as to retain the anchor and the implant with the umbo. The anchor can extend to an opening 30A1 in the flap, for example a hole. Alternatively, the anchor can be affixed to the flap. The anchor may comprise many known biocompatible materials such as biocompatible metals and biocompatible plastics and many combinations thereof. When the anchor is positioned at least partially around the umbo and connected to the implantable device 30D, the flap can be positioned over the bed from which the flap was removed. The positioned flap may extend substantially from the umbo to the device 30D so as to promote healing of the bed of tissue.

Figure 2A:
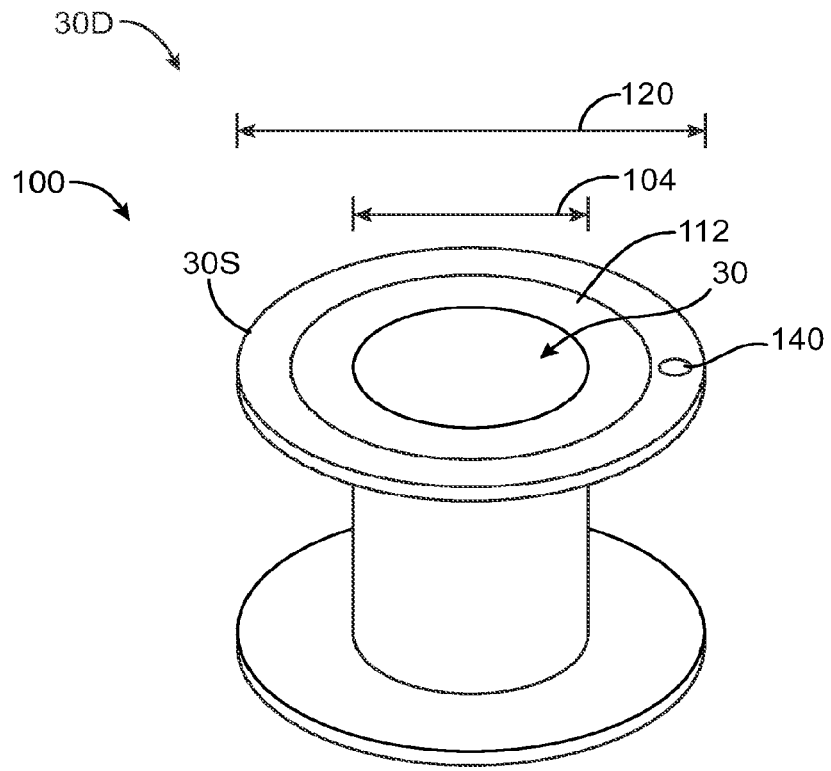
FIG. 2A shows an eardrum implantable device comprising a transducer configured to vibrate the eardrum, in accordance with embodiments.
Figure 2B:
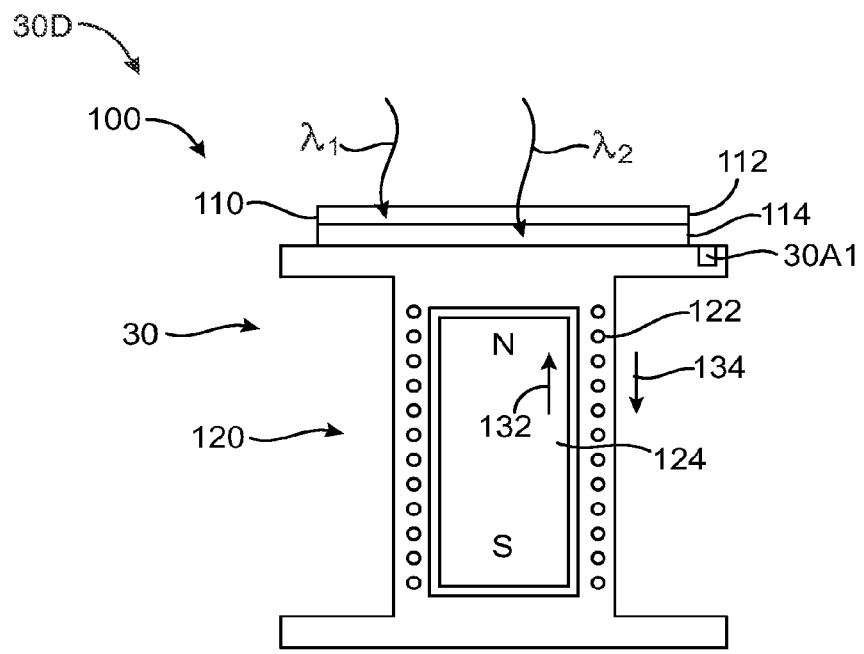
FIG. 2B shows a side cross sectional view of the device as in FIG. 2A.

FIGS. 2A and 2B show an isometric view and a side cross sectional view of an eardrum implantable output transducer assembly 100 in which the eardrum implantable device 30D comprises the output assembly 30. The output assembly 30 may comprise at least one transducer configured to vibrate the eardrum, as described above. The at least one transducer may comprise a magnet positioned within the eardrum implantable device 30D and coupled to an coil, for example an external coil positioned in the ear canal as described above. The at least one transducer may comprise a photodetector configured to vibrate the eardrum in response to an optical signal. For example the at least one transducer may comprise a photostrictive transducer configured to vibrate in response to light energy absorbed with the photostrictive material. The at least one transducer may comprise a first transducer configured to receive electromagnetic energy such as light energy and a second movement transducer coupled to the first transducer such that the second transducer is configured so as to vibrate the eardrum in response to the electromagnetic energy received by the first transducer. The first transducer may comprise at least one photodetector and the second transducer may comprise at least one of a magnet, a coil, a coil and magnet transducer, a piezoelectric transducer, a balanced armature transducer or a magnetostrictive transducer. The output transducer assembly 100 may comprise circuitry coupled to at least one photodetector 110 and configured for support with the eardrum as described in U.S. App. Nos. 61/177,047, filed on May 11, 2009, entitled "Optical Electro-Mechanical Hearing Devices With Combined Power and Signal Architectures"; and 61/139,520, filed on Dec. 12, 2008, entitled "Optical Electro-Mechanical Hearing Devices with Separate Power"; the full disclosures of which are incorporated herein by reference and suitable for combination in accordance with embodiments of the present invention. The input assembly may be configured to produce a light output signal so as to transmit the audio signal. For example, the light output from the input assembly may comprise a first output signal and a second output signal.

The assembly 100 can be configured to vibrate in response to an optical signal. The transducer 120 may comprise a coil 122 and a magnet 124. The coil 122 can be electrically coupled to at least one detector 110. Light absorbed by at least one detector 110 can generate a current in coil 122 such that the magnet and coil are urged in opposite directions. For example, the coil and magnet can urge the magnet in a first direction 132 and the flanges contacting the eardrum and the coil in a second direction 134 opposite the first direction. For example, the transducer may comprise and couple opposing masses so as to induce vibrations of the eardrum as described in U.S. App. No. 61/099,087, filed Sep. 22, 2008, entitled, "Transducer Devices and Methods for Hearing", the full disclosure of which is incorporated by reference and suitable for combination in accordance with embodiments of the present invention. Although reference is made to a coil and magnet, the transducer 130 may comprise one or more of the many transducers as described above.

The light signal may comprise the first light output signal and the second light output signal so as to drive the movement transducer 120 in first direction 132 and second direction 134, respectively. The cross sectional size of both detectors positioned on the assembly may correspond to a size of one of the detectors. The first detector 112 may be sensitive to light comprising at least one wavelength of about 1 um, and the second detector 114 can be sensitive to light comprising at least one wavelength of about 1.5 um. The first detector 112 may comprise a silicon (hereinafter "Si") detector configured to absorb substantially light having wavelengths from about 700 to about 1100 nm, and configured to transmit substantially light having wavelengths from about 1400 to about 1700 nm, for example from about 1500 to about 1600 nm. For example, the first detector 112 can be configured to absorb substantially light at 904 nm. The second detector 114 may comprise an Indium Gallium Arsenide detector (hereinafter "InGaAs") configured to absorb light transmitted through the first detector 112 and having wavelengths from about 1400 to about 1700 nm, for example from about 1500 to 1600 nm, for example 1550 nm. In a specific example, the second detector can be configured to absorb light at about 1310 nm. The cross sectional area of the detectors can be about 4 mm squared, for example a 2 mm by 2 mm square for each detector, such that the total detection area of 8 mm squared exceeds the cross sectional area of 4 mm squared of the detectors in the ear canal. The detectors may comprise circular detection areas, for example a 2 mm diameter circular detector area.

The first photodetector 112 and the second photodetector 114 may comprise at least one photovoltaic material such as crystalline silicon, amorphous silicon, micromorphous silicon, black silicon, cadmium telluride, copper indium gallium selenide, and the like. In some embodiments, at least one of photodetector 132 or photodetector 132 may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications Nos. 61/073,271, entitled "Optical Electro-Mechanical Hearing Devices With Combined Power and Signal Architectures"; and 61/073,281, entitled "Optical Electro-Mechanical Hearing Devices with Separate Power and Signal", the entire contents of which have been previously incorporated herein by reference and may be suitable for combination in accordance with some embodiments as described herein.

The electromagnetic signal transmitted through the eardrum TM to the assembly 100 may comprise one or more of many kinds of signals. For example, the signal transmitted through the eardrum TM may comprise a pulse width modulated signal. The pulse width modulated signal may comprise a first pulse width modulated signal of at least one first wavelength of light from a first source and the second pulse width modulated signal of a second at least one wavelength of light from a second source. The first at least one wavelength of light may be received by a first detector, and the second at least one wavelength of light may be received by the second detector.

FIG. 2B1 shows the assembly 100 and the transducer 120, in which the magnet 124 comprises a pair of opposing magnets. The transducer 120 may extend along an axis 120A, such that the coil 122 and the magnet 124 are aligned with the axis 120A. The coil 122 can be disposed in an outer annular casing and extend around an inner cylindrical portion comprising the magnet 124. The magnet 124 may comprise pair of opposing magnets. The pair of opposing magnets may comprise a first magnet 124A and a second magnet 124B aligned along axis 120A. The first and second magnets can be disposed along the axis 120A such that the magnetic field of the first magnet opposes the magnetic field of the second magnet. The pair of opposing magnetic may increase the efficiency of the transducer and may provide decreased sensitivity to external magnetic fields, for example external magnetic fields that can be a source of noise and external magnetic fields such as with MRI machines.

Figure 2C:
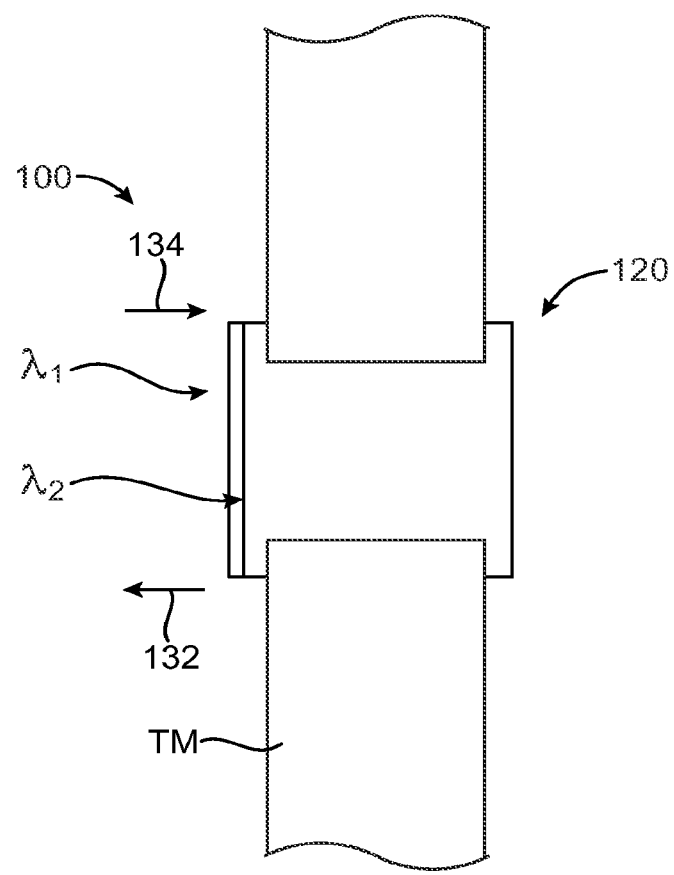
FIG. 2C shows the device as in FIGS. 2A, 2B and 2B1 positioned in the eardrum TM of the user.

FIG. 2C shows the device as in FIGS. 2A, 2B and 2B1 positioned in the eardrum TM of the user. The assembly is configured to move the eardrum TM in the first direction 132 in response to the first at least one wavelength λ1 of the first light output signal and to move the eardrum TM in the second direction 134 in response to the second at least one wavelength λ2 of the second light output signal.

While the above is a complete description of the preferred embodiments of the invention, various alternatives, modifications, and equivalents may be used. Therefore, the above description should not be taken as limiting in scope of the present invention, which is defined by the appended claims.

What is claimed is:

1. A device to transmit a sound to a user having an eardrum and a malleus, the device comprising:
   a retention structure to connect to the malleus;
   a structure configured for placement in the eardrum; and
   a transducer supported with the structure and configured to vibrate the eardrum, wherein the retention structure is sized to extend from the malleus to the structure in order to inhibit migration of the structure when placed in the eardrum.

2. The device of claim 1 wherein the transducer comprises at least one of a magnet, a coil, a coil and magnet transducer, a piezoelectric transducer, a balanced armature transducer, a photostrictive transducer or a magnetostrictive transducer.

3. The device of claim 2 wherein the transducer comprises the magnet and wherein the magnet is configured to vibrate the eardrum in response to a coil positioned in an ear canal of the user.

4. The device of claim 1 further comprising at least one of a coil or at least one photodetector supported with the structure and coupled to the transducer, the at least one photodetector configured to receive electromagnetic energy and vibrate the transducer in response to the audio signal such that the user perceives the sound.

5. The device of claim 4 wherein the transducer comprises a pair of opposing magnets disposed within the coil so as to vibrate the eardrum in response to the audio signal.

6. The device of claim 1 further comprising an anchor configured to anchor the structure to the eardrum.

7. A method of providing a hearing to a user having an eardrum and a malleus, the method comprising:
   providing a hearing device comprising a structure configured for placement in the eardrum; and
   placing the hearing device in the eardrum; and
   attaching a retention structure to the malleus of the user, wherein the retention structure extends from the malleus to the structure in order to inhibit migration the structure in the eardrum.

8. The method of claim 7 further comprising positioning at least one photodetector in a middle ear of the user and wherein the structure is configured to transmit light.

9. The method of claim 7 wherein the structure is configured to support a transducer configured to vibrate the eardrum.

10. The method of claim 7 wherein the retention structure comprises an anchor shaped to attach to the malleus of the user to anchor the structure in the eardrum.

11. The method of claim 10 wherein the anchor is coupled to the structure on a medial side of the structure.

12. The method of claim 7 wherein the eardrum is cut to form a flap on a medial side of the eardrum and wherein the flap is positioned at least partially over the anchor when the anchor is attached to the malleus.

13. The method of claim 7 wherein the structure is positioned in an at least partially inferior and at least partially anterior portion of the eardrum.

* * * * *